(12) United States Patent
Hansen (10) Patent No.: US 6,846,804 B2
(45) Date of Patent: Jan. 25, 2005

(54) CONSTRUCTION OF A STRUCTURAL VARIANT OF SUBLANCIN TO FACILITATE ITS ISOLATION AND USE IN BIOREMEDIATION OF ENVIRONMENTAL CONTAMINATION BY GRAM-POSITIVE SPORE FORMERS SUCH AS *BACILLUS ANTHRASIS*

(75) Inventor: J. Norman Hansen, Silver Springs, MD (US)

(73) Assignee: University of Maryland, College Park Office of Technology Commercialization, College Park, MD (US)

( * ) Notice: Subject to any disclaimer, the term of this patent is extended or adjusted under 35 U.S.C. 154(b) by 0 days.

(21) Appl. No.: 09/894,030

(22) Filed: Jun. 29, 2001

(65) Prior Publication Data

US 2002/0165139 A1 Nov. 7, 2002

Related U.S. Application Data

(60) Provisional application No. 60/215,449, filed on Jun. 29, 2000.

(51) Int. Cl.[7] .................. A01N 37/18; A61K 38/16; A61L 2/16; C07K 14/32
(52) U.S. Cl. ..................... 514/12; 514/9; 530/300; 530/317; 530/324; 530/825
(58) Field of Search ................. 514/12, 9; 530/300, 530/324, 317, 825

(56) References Cited

U.S. PATENT DOCUMENTS 5,218,101 A    6/1993   Hansen ................ 536/23.7
5,516,682 A    5/1996   Hansen ................ 435/252.3
5,576,420 A   11/1996   Hansen ................ 530/324
5,861,275 A    1/1999   Hansen ................ 435/69.1
5,885,811 A    3/1999   Hansen ................ 435/477
6,143,498 A * 11/2000   Olsen et al. ............. 435/6
6,153,405 A   11/2000   Hansen ................ 435/69.1

FOREIGN PATENT DOCUMENTS

WO    WO 00/39152    7/2000

OTHER PUBLICATIONS

Paik et al. 1998. Identification and characterization of the structural and transporter genes for, and the chemical and biological properties of, sublancin 168, a novel lantibiotic produced by *Bacillus subtilis* 168. J. Biol. Chem. 273:23134–23142.*

Hawley et al. 2001. Biological weapons: A primer for microbiologists. Annual Review of Microbiology 55:235–253.*

(List continued on next page.)

*Primary Examiner*—Gabriele Bugaisky
(74) *Attorney, Agent, or Firm*—Arent Fox PLLC (57) ABSTRACT

A sublancin peptide variant having a Gly-His peptide sequence fused to the C-terminal end of the mature sublancin peptide provides an affinity tag facilitating increased purification of the peptide variant from sample preparations without affecting the intracellular processing of the sublancin peptide variant, expression by a host cell or its biological activity in secreted form. This sublancin variant has specific inhibitory activity for spore outgrowth as for the native sublancin peptide. Production of the sublancin peptide variant on an industrial scale is set forth as are methods of decontaminating spore-infected areas. Methods for generating the peptide variant gene, plasmid and transformant are also described.

16 Claims, 6 Drawing Sheets

OTHER PUBLICATIONS

Inglesby et al. 1999 Anthrax as a biological weapon: Medical and Public Health Management. JAMA (Journal of the American Medical Association) 281 (18): 1735–1745.*

Kupke et al. 1997. In vivo reaction of affinity tag labelled epidermin precursor peptide with flavoenzyme EpiD. FEMS Microbiology Letters 153:25–32.*

Callard et al. (1994) The cytokine Factsbook. San Diego:Academic Press p. 22.*

Hansen, "Nisin and Related Antimicrobial Peptides", Biotechnology of Antibiotics, Second Edition, pp. 437–467 (ed) W. Strohl. New York: Marcel Dekker, Inc. (1997).

* cited by examiner

Fig.1

Sublancin 168

Fig.2

Sublancin-His tag

Fig.3

```
                                                                    EcoRI
                    pTZ sequence <---------GAATTCCGGCTCTAAAGCGAT
TCTGAGAGCAGTTTCTTATACACCAGGAGGAACTGCACTTCAACGAGCTGGATTAACAGTGGGCATAAG
AGTTAAGATAAAATTAAACTTATATACAAACATAAGAAAGAGTGATTAATACACGTTTTTTGTTTAAAAACTTAAAAACAT
GGTAAAATTATATAAAAACATAAGAAAGAGTGATTATATGGAATATGTAGTTATGATAATCATTTTATTA
GCACTTTTCTTATTTACTGTTTTCCTAAATACACGTTTATAGTTTTGATGAAAAATGCTTAGTCTTAA
AATTTGGTTTATCTAAAACAGAAATTCCAATTAATACAGTTAGTATTAAAGAGTCAGACAAGTATGG
AGTTGCAGATAATATCGATTATAAATTGTATGCCATATGCTCAACCAGATAGAATTGTTATTGAAACT
ACAAATAAGCGTTTCTAGTTTTTTAAATGGAGCTCAACAATTATTCAAAAGTATAAAAGGGTTAGTG
TTTGAACATAAAAAGTACCTTCTTACAAATATCAAATAATCCATAATGTACTTTTTTGTATCTATATTATTTAGTGTATTACAACCAA
CTAAATTTTATCATTATAATCAAAATAAATCCATAATGTACTTTTTTATTTAGTGTATTACAACCAA
 BamHI  (   ~900 bp  ) BamHI
TTC GGATCC <----cat----> GGATTCGTGTATTACAACCAATTC TGTTTATTGATAGTAATAAA
GTTTTTTCTATGATTATGAACAAGTTTCCTTATAATTTTCAAA
AAAAATAAAAATATGTTGAATTTAGATTTATCTTCCTTATATTAAAAAATGTAATCCGATTGCAA
                                            Xho I
ACAAATGGGAGGTTTACAA ATGGAAAAAGCTATTAAAGAAGTTAAACTCGAGGAACTCGAAAACCAAA
 Sun A                                                            Pst I
AAGGTAGT GGATTAGGAGAAAAGCTCAGTGCTGCCAAAACTATCGTCAATTCTGCAGA TAAAACATTGTAGAGGGAAT
TTGTGGTGGCGAGCTGTGTTGCTTGTCAAAACTATCGTCAATTCTGCAGA TAAAACATTGTAGAGGGAAT ATTTAAATAATTCCCTCATATTTAAAGCGGGACTTGTGTGGATTGAAATTGAATAAGAAAAAAGAAAATATGTTCATACTA
AACAGTTAATGTAATAGTCATGATTGTGGACTAGCTTGGGATCTCGTCAATTTGTATCTCAATTTTAAAGTTTCATAACCTTAACTA
TGGAATTGATTTCTTACTAGACATAAAATAGGCCACTTGGGATAAAGGCTATAGTTTAAGACTTAATTGTTATT
TTTAAGAAGATGGGATAAAATAGGCCACTTGTGAATTGCAAGAAATAAGACATTCGAAGCCTAAAAC
AATAAAAGCTCCCCTTTACTTGTATAGCTTTGTTAGAAGGGAGGAATATGGACATTACATAACAATATACGAAAT
TAGAAAATAACTATTTACTTGTTAGTGATCCTGATAAAGACAAAATAACTAAAATAAAAAAGAGATTTT
GAAAGTAAATTCACAAACTTTTATATTAAGGACATACTTTTAGAAATAAATTGATCGTTTTTGTGATTTATTGAC
AAAAACATTCTTACTTTTCGTTGTGGGTCCTGCTGAAGCTT------>pTZ sequence
                                     HindIII
TTCCTTGTTCGTTGTGGGTCCTGCTGAAGCTT
```

Fig.5A

B. subtilis E∆Sun

B. subtilis 168

Fig.5B

B. subtilis 168 SunA'

Fig.6

```
     pLPcat                          Sublancin leader →
TTGCAAACAAATGGGGAGGTTTTACAA  ATGGAAAAGCTATTTAAAGAAG
                             MetGluLysleuPheLysGluV XhoI                              sublancin prep-
TTAAACTCGAGGAACTCGAAAACCAAAAAGGTAGT  GGATTAGGAAAAGC
AlLysLeuGluGluLeuGluAsnGluLysGlySer  GlyLeuGlyLysAl tide →
TCAGTGTGCTGCGTTGTGGCTACAATGTGCTAGTGGCGGTACAATTGGTT
aGlnCysAlaAlaLeuTrpLeuGlnCysAlaSerGlyGlyThrIleGlyC KasI
GTGGTGGCGGCGCCGTTGCTTGTCAAAACTATCGTCAATTCTGTAGAGGT
ysGlyGlyGlyAlaValAlaCysGlnAsnTyrArgGlnPheCysArgGly His Tag →           Stop     PstI
GGTGGTCATCATCATCATCATCATTAGAGTCCTGCAGATAAAACA
GlyGlyHisHisHisHisHisHis  *           pLPcat →
```

CONSTRUCTION OF A STRUCTURAL VARIANT OF SUBLANCIN TO FACILITATE ITS ISOLATION AND USE IN BIOREMEDIATION OF ENVIRONMENTAL CONTAMINATION BY GRAM-POSITIVE SPORE FORMERS SUCH AS *BACILLUS ANTHRASIS*

This application claims priority under 35 U.S.C. §1.119(e) to provisional application Ser. No. 60/215,449, filed Jun. 29, 2000.

This invention was made with Government support under Contract No. AI24454 awarded by the NIH.

FIELD OF THE INVENTION

This Invention relates to the construction and expression of a sublancin analog containing a His-tag and uses thereof.

BACKGROUND OF THE INVENTION

Sublancin 168 was originally discovered in the laboratory of this Inventor. The structure of sublancin and its chemical, physical, and biological properties have been published (3). Properties of sublancin that are relevant to this invention are that it is highly active toward inhibition of outgrowth of spores of Bacillus, and that it is extremely stable and resistant to both chemical and proteolytic degradation. The natural spectrum of antimicrobial activity of sublancin embraces many human pathogens, such as strains of *Bacillus*, *Enterococcus*, *Lactococcus*, *Listeria*, and *Staphylococcus*; and therefore includes *Bacillus anthrasis*, which is the causative agent of the often-fatal disease called anthrax.

Outbreaks of anthrax occasionally occur as a consequence of the death of an infected farm animal, which may result in the spread of *B. anthrasis* spores over an extended area. Such spore contamination can persist for a very long time, since the spores are in a highly stable dormant state. Whereas these natural outbreaks of anthrax can be controlled by good public health practices, a much greater risk exists because of the fact that *B. anthrasis* spores are one of the most attractive candidates as a bio-warfare agent, especially in the hands of a terrorist group. A few pounds of spores, scattered by an appropriate explosive device, could render an extended area uninhabitable for an indefinite period of time. An ideal counter-measure to such an attack would be a substance that could effectively block the outgrowth of the *B. anthrasis* spores, and thereby prevent their ability to cause anthrax infections.

Sublancin 168 is highly effective in its ability to inhibit spore outgrowth, and it is an ideal countermeasure to anthrax, as well as other pathogenic spore-formers. However, in order to perform this role, it is necessary to produce sublancin in large quantities. Even though it is highly effective, its use as a countermeasure would require spraying a solution of sublancin over the entire area that is encompassed by the contamination. In order for this to be practical, it is necessary to be able to produce substantial quantities of sublancin at a reasonable cost.

Sublancin is a natural product of *B. subtilis* 168, and when it is synthesized by the bacterium, it is secreted into the medium. Although sublancin is produced efficiently by the organism, a major factor in the cost of sublancin production is the cost of recovery of the sublancin from solution. Therefore, the development of an efficient method of recovery of sublancin from the culture supernatant would have a major impact on the cost of sublancin production, and therefore on the practicality of its use as a countermeasure against anthrax and other environmental contamination by spores of Gram-positive bacteria.

SUMMARY OF THE INVENTION

An object of the invention is the construction of a His-Tag labeled sublancin peptide.

Another object of the invention is a method for expressing a His-Tag labeled lantibiotic by a susceptible bacterial host strain.

Another object of the invention is the use of the His-Tag label to isolate sublancin directly from growth medium.

Another object of the invention is a method for decontaminating a bacterial spore-infected area.

BRIEF DESCRIPTION OF THE FIGURES

FIG. 3. Sequence of the EcoRI-HindIII insert of the pLPVc integrative plasmid used to delete and replace the natural sunA gene with a mutagenized sunA gene in the *B. subtilis* 168 chromosome. A cat gene has been inserted at an engineered BamHI site to provide a selective marker. An XhoI site has been engineered into the sunA leader region, by means of a silent mutation, to facilitate the construction of structural mutants. The PstI site at the 3' end of the sunA gene is a natural restriction site. The EcoRI-HindIII fragment is cloned into the EcoRI and HindIII sites of the pTZ mps (SEQ ID NO. 1).

FIG. 4. Strategy for the construction of the host-vector pair used to make sublancin mutants. Plasmid pLPHerm was linearized and transformed into wild-type *B. subtilis* 168. Double recombinants in which the SunA ORF was replaced by an erm gene and the ΔsunA ORF were selected on erythromycin plates. These mutants, which are erythromycin resistant and encode a defective SunA peptide, were characterized as shown in FIG. 4. One of the mutants was selected and designated as *B. subtilis* LPeΔsunA.

DETAILED DESCRIPTION OF THE INVENTION

The present invention explores the contribution of an C-terminal affinity tag sequence in purifying a sublancin peptide by the construction and expression of a sublancin-spacer-tag chimera containing the sublancin structural region fused to an affinity tag sequence. The inventors have discovered that an affinity tag, more preferably a His-Tag sequence does not interfere with the bioprocessing of sublancin in a host cell or affect the lantibiotic activity for the mature sublancin protein, and can be used to facilitate purification of a soluble, biologically active sublancin protein.

The term "gene" refers to a polynucleic acid or a nucleotide which encodes a peptide, a prepeptide, a protein or a marker, or to a vector or plasmid containing such a polynucleic acid or nucleotide.

A "chimera" refers to a fusion peptide or protein which is comprised of a part from a first peptide or protein, and a part from one or more additional proteins or peptides.

A "mutant" gene or peptide refers to a gene having a sequence in that one or more bases or residues are deleted, substituted or added at any position therein, including either terminus.

In the present application, "biological activity" refers to activity against a preferably nucleophilic target molecule. Biological activity includes but is not limited to activity against or for modifying enzymatic activity of an enzyme, inhibiting proliferation or growth of an infectious particle or a cancer cell, or blocking the binding of a ligand to its receptor. Most preferably the activity is against Bacillus cereus spores and/or vegetative cells. Preferably, biological activity against Bacillus cereus spores is measured using the "halo assay" described in the experimental section hereunder.

The present invention concerns nucleotides, vectors and constructs encoded thereby, which encode a chimeric or mutant sublancin polypeptide of the formula:

(sublancin)-(spacer)-(tag).

Most preferably, the sublancin is sublancin 168.

The present construct includes a peptide spacer comprising from 1 to 40 amino acids, preferably 1–15, most preferably 1–5. The amino acid is preferably nonpolar, and preferably is one or more amino acids selected from the group consisting of glycine (G or Gly), alanine (A or Ala), valine (V or Val), isoleucine (I or Ile) and leucine (L or Leu). Preferably the amino acid is glycine. The spacer is designed to allow the tag to be freely available for binding, but to reduce susceptibility of the tag to proteolysis by host proteases.

The present construct also encodes a tag sequence comprising an affinity tag including but not limited to FLAG peptide, myc, calmodulin binding peptide, alkaline phosphatase, glutathione S-transferase, β-galactosidase, or histidine. An affinity tag labeled protein can be purified by protein affinity chromatography designed to selectively capture the tagged protein.

Whereas affinity tag labeling of polypeptides is well recognized, before the present invention there was a significant technical barrier to its use for end-labeling sublancin and other antimicrobial peptides of the antibiotic family. The reason is that these peptides undergo extensive post-translational modification as part of their biosynthetic pathway, and it could not have been predicted that His-Tag labeled lantibiotics could be processed into functional, secreted proteins.

The cellular machinery that performs these post-translational modifications must recognize the antibiotic precursor, bind to it, and perform the modifications. Any changes to the precursor protein that interfere with the recognition, binding, or modification steps cannot be utilized. For example, certain modifications to the C-terminal end of the subtilin prepeptide, which is a lantibiotic produced by B. subtilis, resulted in aborting the biosynthetic pathway. Accordingly, His-Tag labeled forms of subtilin were not obtainable (4).

Figure 1:
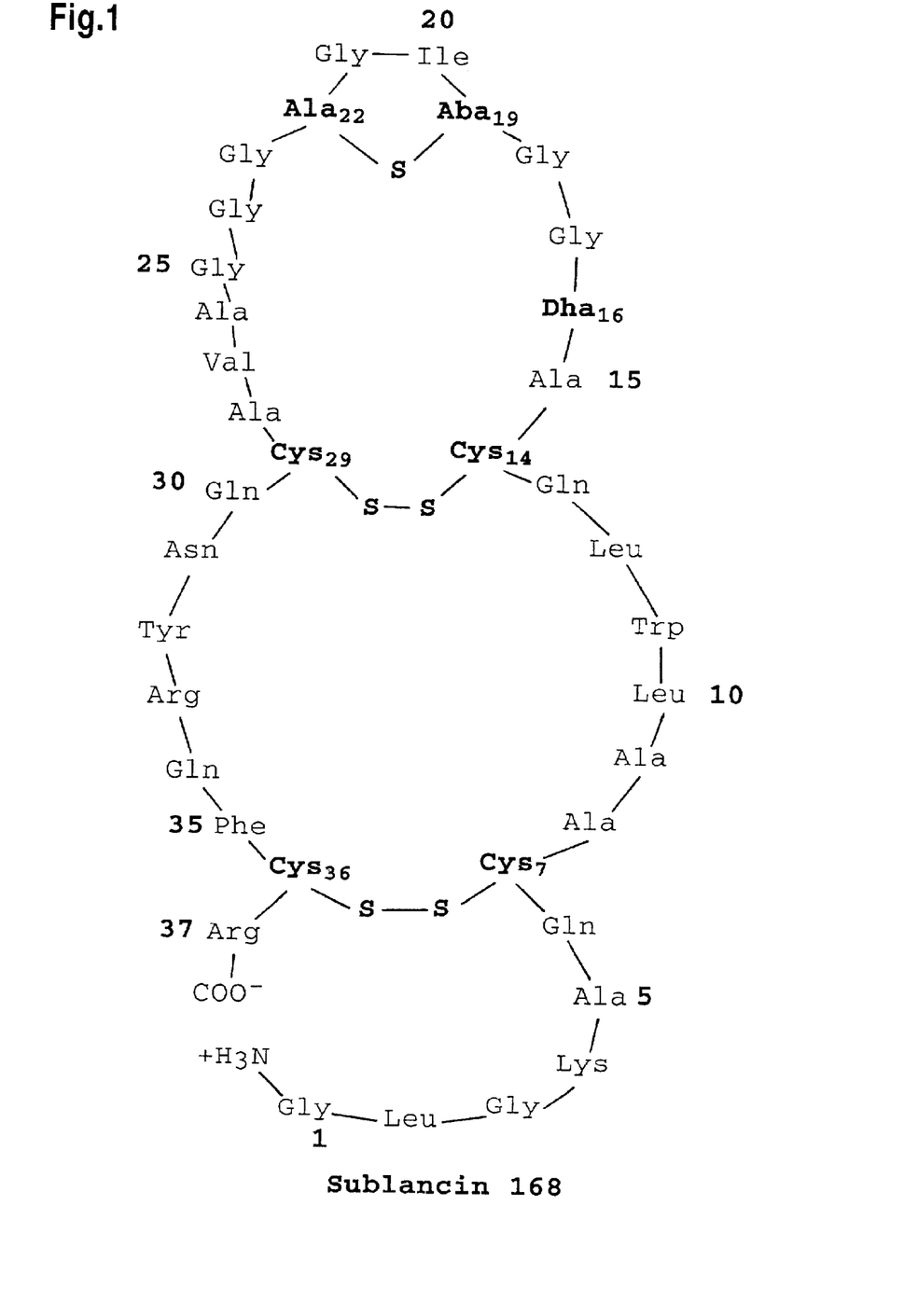
FIG. 1. Structure of sublancin 168.

Sublancin 168 is a antibiotic that was discovered in the laboratory of this Inventor, the structure of which is shown in FIG. 1.

Sublancin has attributes that make it suitable for this invention, which brings together two aspects of sublancin.

The first is that Sublancin 168 is a very powerful inhibitor of bacterial spore outgrowth (3). Sublancin is a lantibiotic that is endogenous to the gram-positive bacterium Bacillus subtilis 168, which is a bacterial strain that has been intensely studied. The complete sequence of its genome is known, and excellent tools for genetic manipulation are available. Strain 168 is non-pathogenic, and has been widely used for industrial production of genetically-engineered biomaterials. The natural level of sublancin 168 production by strain 168 is good (3), which facilitates efficient production of the derivatives.

Sublancin 168 is highly stable, with respect to chemical stability, stability against proteases, and stability against loss of biological activity. This natural stability makes sublancin very well-suited to uses such as against environmental contamination by bacterial spore-formers, which persist for an extended period of time. Because sublancin is also stable, it retains its activity long enough to exert a continued protective effect.

This invention relates to the construction of a sublancin mutant containing a C-terminal His-Tag, and the use of this His-Tag in the isolation of sublancin directly from cultured growth medium. Because of the overall technical difficulty in constructing lantibiotic peptides having an affinity tag, the success in achieving affinity-tag labeling of a sublancin protein constitutes an invention of substantial usefulness. Moreover, since His-Tag labeling of other lantibiotics such as subtilin was unsuccessful, the fact that the inventor succeeded in labeling sublancin with His-tag was unpredictable from previous studies.

A spacer comprising from 1 to 15 amino acid residues is preferable. Two to five amino acid residues as the spacer is more preferable, and three glycine residues is most preferable. Three residues is long enough to reduce interference with the post translational modification machinery, but short enough to minimize the likelihood of non-specific proteolytic cleavage of the His-Tag extension.

Preferably, the affinity tag is histidine (His-Tag), and the histidine tag should be short so as not to alter the conformation of the tagged protein nor should it be involved in artifactual interactions. A His-Tag of 2–10 histidine residues is preferable, a stretch of 2 to 8 histidine residues is more preferable, and a stretch of 2–6 histidine residues is most preferable. Six histidine residues provides excellent binding affinity to nickel which can be used in column purification of a His-Tag labeled protein as described hereunder. An affinity column can be prepared from a nickel-coated solid support such as a plastic or magnetic bead.

Figure 2:
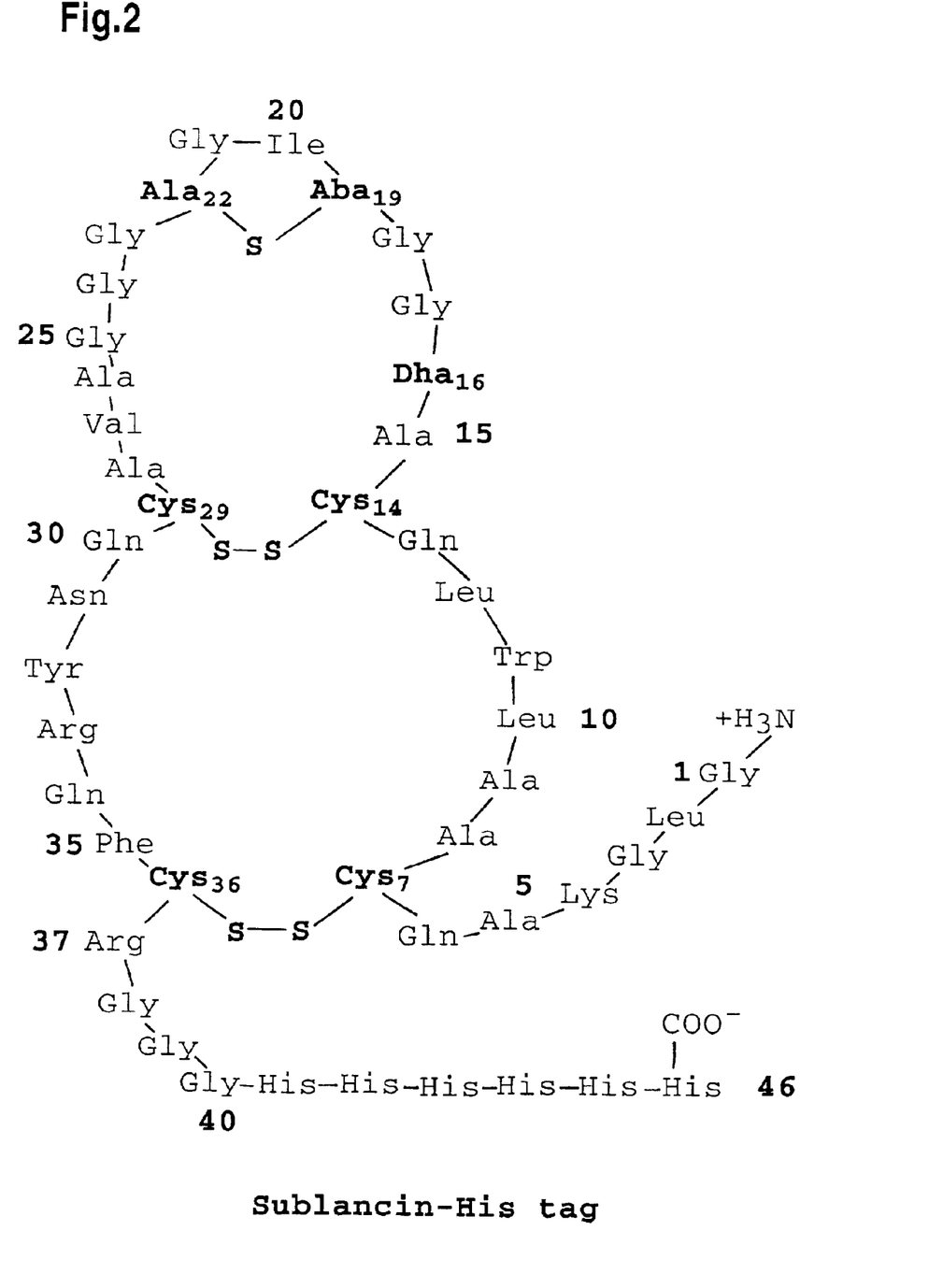
FIG. 2. The design of an affinity tag for subtilin.

In a preferred embodiment, FIG. 2 shows that the sublancin prepeptide has been modified at the C-terminus to contain a spacer followed by a His-Tag affinity group. Specifically, a spacer of 3 glycine residues and a tag of 6 histidine residues have been added to the 37-residue sublancin peptide.

Production of purified, active sublancin protein at an industrial level is now achievable with a His-Tag labeled sublancin protein. It is possible to put sublancin into practical use in medical, industrial and consumer products. Uses of sublancin include but are not limited to a food preservative, an antimicrobial agent or a decontaminating agent.

Accordingly, an object of the invention is a method for decontaminating a bacterial spore infected surface area. For decontamination, a spore-inhibiting effective amount of sublancin can be applied to the contaminated area. A contaminated area includes but is not limited to any solid surface having been in contact with an infectious particle. The decontamination is preferably for external use.

The sublancin can be diluted in any phosphate buffered solution of pH 6.0, for example, at an effective concentration in the range of 0.01 µg/ml to 10 µg/ml, more preferably, 0.2 µg/ml to 1 µg/ml.

For decontamination of large areas such as a field or ground space where the wetness of soil conditions may be variable, achieving a final, uniform concentration of 1 µg/ml is preferable.

Application of the sublancin solution to a surface area can occur by spraying under conditions which do not change the functional characteristics of the sublancin protein.

The construction, expression and affinity purification of a His-Tag labeled sublancin protein is described by way of the following non-limiting examples.

EXAMPLE 1

Design of the Gene Sequence To Express the His-tag Polypeptide

The strategy that was developed for sublancin mutagenesis is the subject of a previous provisional patent application Ser. No. 60/215,449. It is similar to the strategy used for subtilin mutagenesis (2); namely, to construct a host-vector pair, with the vector being a plasmid for use in the construction and propagation of the mutant gene, and the host being a *B. subtilis* 168 mutant with a deletion in the sublancin gene and an erm resistance marker. The plasmid vector was designed to contain homologies to the regions flanking the sublancin gene together with a cat selective marker, such that a double-recombination between the plasmid and the host results in replacement of the erm gene in the host with the mutagenized sublancin gene, together with the cat marker. After this recombination, the mutagenized sublancin gene is located precisely where the native gene had been, so that effects on expression would be minimized. Appropriate recombinants are identified by their loss of erythromycin resistance, and gain of chloramphenicol resistance.

Bacterial strains, cloning vectors, and culture conditions. Bacterial strains and cloning vectors are listed in Table I. Sublancin and its analogs were expressed and isolated as previously described (3). Competent *B. subtilis* 168 cells were prepared according to Young and Wilson (6).

TABLE I

| Bacterial Strains Strain | Description | Source |
|---|---|---|
| BR151 | Wild type *Bacillus subtilis* 168 | BGSC[a] |
| *B. subtilis* LPeΔsunA | *Bacillus. subtilis* 168 in which the sublancin gene contains an in-frame deletion, and an erm selective marker | Invention |
| *B. subtilis* sunA' | Sublancin producer strain made by transforming pLPVc into *B. subtilis* LPeΔsunA | Invention |
| JM109 | Standard *E. coli* cloning strain | Life Tech.[b] |
| JM101 | Standard *E. coli* cloning strain | Life Tech.[b] |
| *B. cereus* T | Strain used to assay sublancin | BGSC |

TABLE I-continued

| Cloning Vectors Plasmid | Description | |
|---|---|---|
| pSUB8kb | An 8kb fragment from *Bacillus subtilis* 168 containing the sublancin gene in pTZ18R | Ref[c] |
| pTZ18R | Standard cloning vector | USB[d] |
| pLPeΔsunA | Plasmid used to construct *B. subtilis* LPeΔsunA | Invention |
| PLPc | Plasmid used to integrate a sublancin gene into the chromosome of *B. subtilis* LPeΔsunA | Invention |

Bacterial strains and plasmids used in this work.
[a]Bacillus Genetics Stock Center, University of Ohio, Columbus OH.
[b]Life Technologies, Gaithersburg MD.
[c](4).
[d]United States Biochemical Corp., Cleveland OH.

Cloning by PCR. The polymerase chain reaction (PCR) was used to generate the DNA fragments used for the construction of the plasmid vectors used for mutagenesis. Plasmid pSUB8kb was used as the template DNA for the PCR reactions. The sequences of the oligonucleotides used as primers in the PCR reactions are listed in Table II, and the template regions corresponding to these oligonucleotides are identified in FIG. 3. The reactions were performed using pfu DNA polymerase (Stratagene, La Jolla, Calif.) during 30 cycles of denaturation at 95° C. for 30 sec, annealing at 50° C. for 90 sec, and extending at 72° C. for 3 min. The PCR fragments were cleaved with EcoRI and HindIII and cloned into the EcoRI-HindIII site of pTZ, which was propagated in *E. coli* JM101 or JM109. The PCR primers were designed in such a way that the plasmid constructs could be assembled by a sequence of ligation and cloning steps that added one PCR segment at a time, with each addition being confirmed by cloning and restriction analysis before adding the next segment. After the assembly was complete, the entire insert was subjected to dideoxy sequence analysis to confirm that it had been correctly assembled and that it contained no unintended mutations.

TABLE II

|   | Oligonucleotide Sequence written 5' to 3' |
|---|---|
| LPHF1 | GACTGAATTCCGGCTCTAAAGCGATTC |
| SEQ ID No. 3 | EcoR1 |
| LPHR1 | GGACTAAGCTT GGATCCGAATTGGTTGTAATACAC |
| SEQ ID No. 4 | HindIII   BamHI |
| LPHF2 | GCAACGAATTC GGATCCGTGTATTACAACCAATTC |
| SEQ ID No. 5 | EcoRI   BamHI |
| LPHR2 | TCGAAAAGCTT GTTAACCTTTTCCATTTGTAAAACC |
| SEQ ID No. 6 | HindIII   HincII |
| LPHF3 | TGGCAGAATTC GTTAACTATCGTCAATTCTGC |
| SEQ ID No. 7 | EcoRI   HincII |
| LPHR3 | GGAGCAAGCTT CAGCAAGACCCACAACG |
| SEQ ID No. 8 | HindIII |
| LPVF2 | Same as LPHF2 |
| SEQ ID No. 9 | |
| LPVR2 | GGATGAAGCTT CTCGAGTTTAACTTCTTTA |
| SEQ ID No. 10 | HindIII   XhoI |
| NLPVF3 | GTAGGAATTC CTCGAGGAACTCGAAAACC |
| SEQ ID No. 11 | EcoRI   XhoI |
| LPPMR2 | GGAGCAAGCTTTTATCTGCAGAATTGACGATAG |
| SEQ ID No. 12 | HindIII   PstI |
| LPVF4 | GATTGAATTCGGCGCCGTTGCTTGTCAAAAC |
| SEQ ID No. 13 | EcoRI |
| LPVR4 | Same as LPHR3 |
| SEQ ID No. 14 | |

TABLE II-continued

Oligonucleotide Sequence written 5' to 3'

| | |
|---|---|
| L13 | GTGTATTACAACCAATTCTG |
| SEQ ID No. 15 | |
| L15 | TTGTGGCTACAATGTGCTAG |
| SEQ ID No. 16 | |

Sequences of Oligonucleotides used for PCR and sequencing primers and hybridization probes. The locations of the template regions corresponding to the primers are shown in FIG. 3. LPV oligos were used to construct the pLPc mutagenesis vector, and the LPH oligos were used to construct the pLPeΔsunA plasmid, which was used to construct B. subtilis LPeΔsunA. LPVF and LPHF oligos prime in the forward direction, and the LPVR and LPHR oligos prime in the reverse direction. Oligonucleotide L13was used as a sequencing primer that was about 220 nt upstream of the sublancin gene, and L15 was used as a hybridization probe within the sublancin gene.

A. Construction of pLPVc Vector by PCR Cloning

The primary vector, pLPVc, was constructed from components synthesized by PCR and assembled in the EcoRI-HindIII site of the E. coli plasmid pTZ. The complete assembled EcoRI-HindIII insert sequence of pLPVc is shown in FIG. 3. This insert contains a 650 base pair upstream chromosomal homology, followed by a cat gene that has been inserted into an engineered BamHI site, followed by the presublancin (sunA) gene, which contains a translationally-silent XhoI site in the leader region of SunA, and the natural PstI site in the C-terminal region, which is followed by a 650 base pair downstream chromosomal homology. This plasmid constitutes a cassette-mutagenesis system, in which the sequence of the mature region of SunA can be modified by replacing the XhoI-PstI fragment with a mutagenized sequence.

B. Construction of the B. Subtilis LPeΔsunA Host

The pLPVc plasmid was then modified in order to construct pLPHe, which was used to engineer a deletion in the chromosomal sunA gene and replace the cat gene with an erm gene. The pLPHe plasmid, shown in FIG. 4, contains an erm gene in the BamHI site, and 47 codons are removed from the central region of the 56-codon sunA ORF. The remaining 9 codons are in-frame in order to minimize any effects of the deletion on the expression of downstream genes that may be required for sublancin biosynthesis. This in-frame construction was to permit this host to be used for expression of sublancin genes in trans, from a plasmid, as well as by integration into the chromosome.

Figure 4:
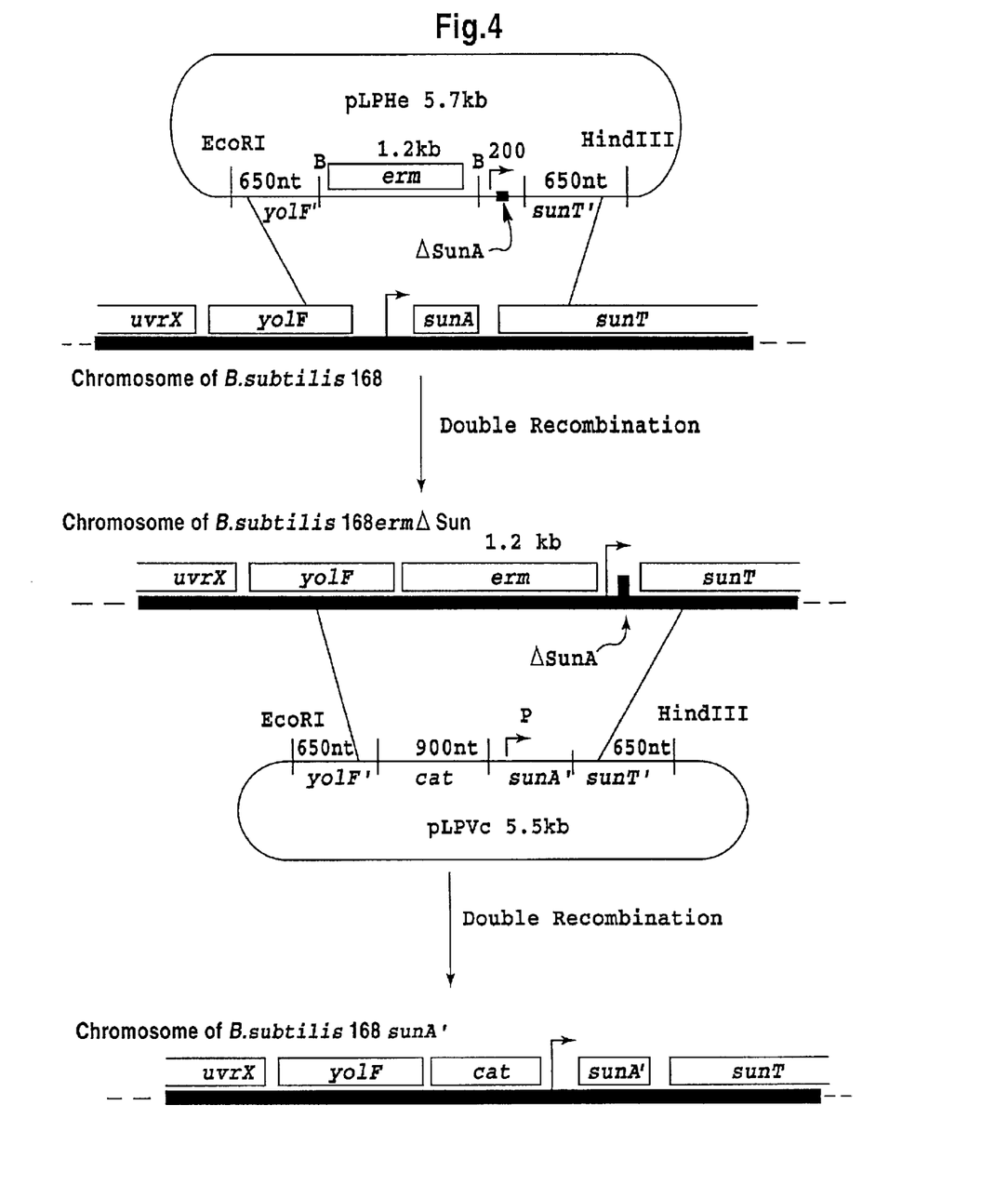

The use of these plasmids in making sublancin mutants is diagrammed in FIG. 4. First, a double-recombination between pLPHe and the B. subtilis 168 chromosome replaces the sunA gene with an erm gene. The resulting B. subtilis LPeΔsunA is erythromycin resistant and does not produce sublancin. The pLPVc plasmid was then used to introduce a mutagenized copy of sunA, at precisely the same location occupied by the original sunA gene by means of a double-recombination that replaces the erm gene and sunA deletion with a cat gene and the mutant sunA' gene. The cat gene is placed upstream from the sunA' promoter so as to not interfere with expression of the sunA' gene.

A halo assay was used to compare the amount of antibiotic production by B. subtilis 168 with that of the LPeΔsunA deletion strain. The amount of antibiotic activity produced by a bacterial colony was determined by its ability to inhibit outgrowth of Bacillus cereus T spores to produce a halo around the colony. B. cereus T spores were prepared by suspending 250 mg of lyophilized spores (7), in 30 ml of sterile water and subjecting them to heat shock for 2 hr at 65° C. The spores were centrifuged and resuspended in 50 ml of 10% ethanol. This solution was used to spray Medium A plates on which colonies had grown to a diameter of 1 mm. The plates were incubated 5 to 12 hr to allow the spores to germinate and outgrow. The diameters of the clear halos were used to compare the amount of antibiotic produced by the colonies.

Figure 5A:
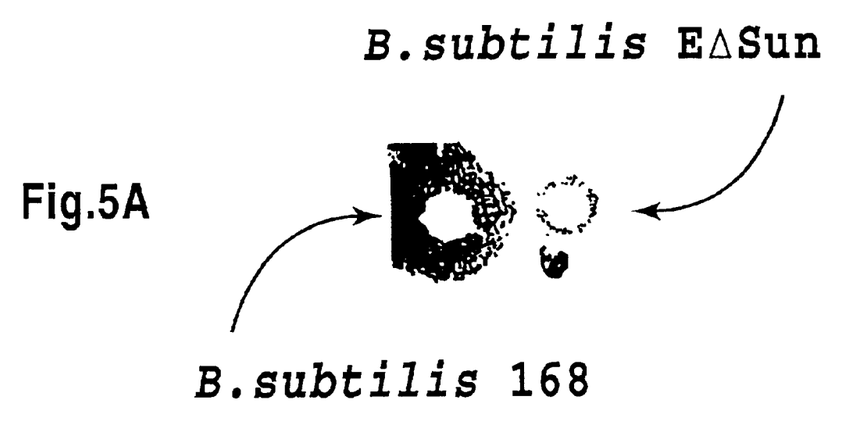
FIG. 5. Lack of sublancin production in *B. subtilis* EΔSun, and its restoration by integration of the sunA' gene. Panel A. Halo assay showing sublancin production from wild-type *B. subtilis* 168, compared to the EΔSun deletion strain. Panel B. Halo assay showing production of sublancin after restoration of the sublancin gene as sunA', which has translationally-silent mutations.
Figure 5B:
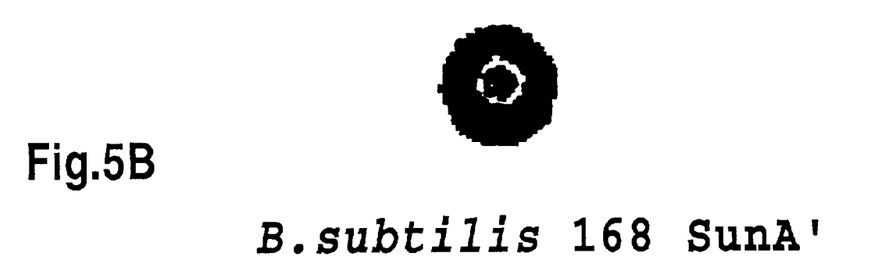

As shown in FIG. 5, the difference is dramatic, with the wild-type strain giving a large halo, and the deletion strain a barely detectable one. Under these growth conditions, sublancin constitutes a large majority of the antimicrobial activity produced by B. subtilis 168.

C. Integration of the SunA' Gene Restores Sublancin Biosynthesis.

The sublancin gene subcloned into the plasmid pLPVc is sunA', which is identical to sunA except for the translationally-silent mutations used to create the XhoI site. Since sunA' encodes the same amino acid sequence as the natural sunA gene, placing sunA' into the chromosome at the location originally occupied by sunA would be expected to restore sublancin production. FIG. 5 shows a halo assay demonstrating that recombinant cells having the sunA' gene integrated into the chromosome are restored in their expression of antimicrobial activity.

The molecular mass of sublancin was determined using electrospray ionization mass spectroscopy (ESI-MS) on a single quadropole ion-trap mass spectrometer in positive ion mode (LCQ, Finnigan, San Jose, Calif.). The source conditions were as follows: sheath gas flow, 40 units, ESI spray voltage, 5 kV, capillary temperature 200° C., capillary voltage 46 V. MS data were acquired on a Windows NT worksation running the LCQExplore software package (Finnigan). MALDI-TOF MS were carried out in positive-ion mode (Proflex, Bruker, Manning Park, Mass.). Sinapinic acid, dissolved in acetonitrile, 0.1% TFA (3:7), was used as matrix. The sample and matrix were applied to the sample target (Bruker) according to the sandwich method of Kussman et al. (8). Tryptic digest fragments were sequenced using tandem MS/MS, using the nanospray adapter on the Finnigan LCQ (nanoESI-MS/MS). Nanospray capillaries (Protana, Odense, Denmark) were used to supply the sample to the LCQ at a very low flow rate (1–10 nl/min). The source conditions were as follows: ESI spray voltage, 0.8–0.1 kV, capillary temperature 200° C., capillary voltage 41 V, MS/MS relative collision energy, 80%. Sequence interpretation was assisted by the use of AminoCalc software (Protana).

The active peak emerged from the HPLC column at the same gradient position as natural sublancin (data not shown), and mass spectral analysis using MALDI-TOF gave a major species with a molecular mass of 3881 Da. The molecular weight species corresponded to the 3881 Da positive control using natural sublancin. This molecular weight is also very close to the 3878 molecular weight previously reported for sublancin (6). These results demonstrate that B. subtilis LPeΔsunA host has been stably converted to express sublancin by the pLPVc plasmid, and that the presence of the cat gene upstream from the sunA gene does not interfere with sunA expression.

EXAMPLE 2

Construction of Sublancin with a 3-residue Gly Spacer and a 6-Residue His-Tag at the C-terminal End of Sublancin.

Figure 6:
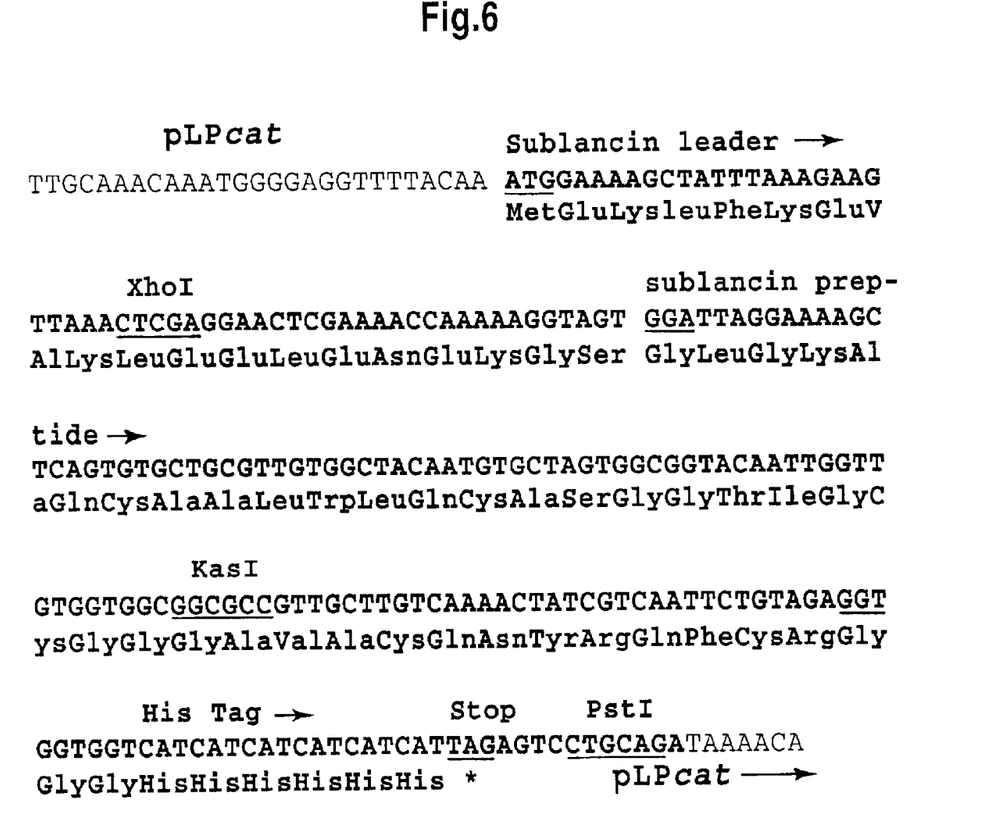
FIG. 6. The sequence of the gene for sublancin His-Tag. The reading frame of the sublancin-His Tag gene and the sequence of the peptide sequence the gene codes for are highlighted in bold (SEQ ID NO. 2). Also highlighted are the restriction sites as well as the leader peptide, sublancin prepeptide, the 3-Gly linker, and the 6-His Tag. The sequences flanking the gene correspond to those of the mutagenesis cassette vector pLPcat.

FIG. 2 shows the sequence of the desired peptide. In order to produce this peptide, it is necessary to construct a mutagenesis vector that encodes this sequence, insert the sequence into the chromosome by the strategy described above, and allow the peptide to be expressed by the cell. The gene sequence that was designed and constructed is shown in FIG. 6. This sequence was constructed in the pLPcat vector shown in FIG. 4, and transformed into the chromosome of the *B. subtilis* 168 ermΔSun host, as shown in FIG. 4.

EXAMPLE 3

Expression of the Sublancin-Gly-His-Tag Peptide.

The transformed host was cultured in Medium A (1) to allow the Sublancin-Gly-His-Tag polypeptide to be expressed. The culture was grown for 26 hr, which was previously shown to provide optimal expression of the wild-type sublancin peptide. Expression was monitored by observing the appearance of the Sublancin-HisTag polypeptide in the extra cellular medium.

The sublancin-Gly-His-Tag polypeptide was recovered from the extra cellular medium by passing it through a 1×8 cm Hydrophobic Interaction column as previously described for sublancin (3), and eluting with 50% acetonitrile. This was lyophilized and redissolved in 20 ml of 300 mM NaCl, 5 mM imidazole, and 50 mM Tris, pH 7.5 and applied to a 0.5×4 cm Ni-NTA-agarose column (Qiagen). The column was then washed with the same buffer to remove unbound material. The Sublancin-His Tag was then eluted with the same buffer except the imidazole concentration was increased to 250 mM. The first 10 ml of the eluate was lyophilized and resuspended in 2 ml of water to which sufficient trifluoroacetic acid was added to reduce the pH of the final solution to 2.5. This solution was desalted and further purified by applying it to an analytical reversed phase C18 column and eluting it with an acetomtrile-0.05% TFA gradient as previously described (3).

EXAMPLE 4

Species in the HPLC Fractions had Molecular Weights that Corresponded to His-Tag Labeled Forms of Sublancin.

Fractions were lyophilized and redissolved in water; and then subjected to mass spectrometric analysis using MALDI-TOF mass spectrometry. Several different species were observed in fractions 12–14 that eluted from the RP-HPLC column. It is to be noted that the Sublancin-His Tag structure that was actually encoded in the gene was Sublancin-3×Gly-6×His. However, the fractions that eluted from the HPLC column contained very little of the molecular species that corresponded to this expected product. Although there was only a small amount of this expected product, there was some, which indicated that the Sublancin-3×Gly6×His gene construct was intact and functional, and that the gene product was being expressed and secreted into the extracellular medium. Consideration of the other species in these fractions established the strong likelihood that they consisted of various forms of His-tagged sublancin in which one or more of the His residues had been hydrolyzed off. The most abundant of these corresponded to Sublancin-3×Gly-2×His and Sublancin-3×Gly-3×His, and somewhat less of Sublancin-3×Gly-4×His. It is a common observation that in order to bind to a Ni-NTA column, all that is required is a 2×His segment at the C-terminal end of a polypeptide. The result here is consistent with this, and argues that the Ni-NTA column has recovered all those species that have two or more Histidines.

The possibility that there had been significant quantities of polypeptide that contained less than 2×His was considered. This was explored by doing mass-spectroscopic analysis of the total material that eluted from the Hydrophobic Interaction column. This HI column binds sublancin very efficiently, in that it is routinely used to recover sublancin from culture supernatants (3). MALDI-TOF analysis of the eluate from the HI column revealed no detectable amounts of sublancin species that corresponded to cleavages anywhere other than within the 6×His region. That is to say, there was no unmodified sublancin, nor a form of sublancin with Gly segments attached, nor any Sublancin-3×Gly-1× His. The only forms that appeared in the eluate from the HI column corresponded exactly to the forms that appeared from the Ni-NTA column, namely Sublancin-3×Gly-2×His and Sublancin-3×Gly-3×His in the most abundant amounts, substantial amounts of Sublancin-3×Gly-4×His, and some Sublancin-3×Gly-6×His.

EXAMPLE 5

The Histidine Tag does not Interfere with Post-translational Modifications or Biological Activity.

This experiment confirmed that the placement of the His-tag on the sublancin prepeptide does not interfere with the maturation of presublancin into its mature form, which involves the dehydration of the Serine residue at position 16, the dehydration of the Threonine residue at position 19, and the formation of the thioether cross-link between CYS16 and the dehydrobutyrine at position 19. This was determined from the molecular masses of the isolated products. For example, if either or both of the dehydration reactions do not occur, the products will be 18 or 36 Da heavier, respectively, than if they do not occur. Inspection of the molecular masses of the species from the Ni-NTA column were consistent with the dehydrations having occurred in all cases, and it was concluded that the presence of the 3×Gly-6×His C-terminal extension did not interfere with the post-translational processing of the presublancin moiety into sublancin.

That the maturation process had occurred was further confirmed by examining the biological activity of the His-tagged species that eluted from the Ni-NTA column. This was done using a standard assay (3), in which dilutions of the antimicrobial peptide were spotted onto a nutrient agar plate, and the plate is then sprayed with a suspension of *B. cereus* T spores. The plates were incubated for 12–18 hr, whereupon the spores germinated and grew. Sublancin inhibits spore germination, and therefore resulted in a clear halo that was surrounded by a lawn of vegetative cells. The Sublancin-His Tag peptides gave halos that had the same size and appearance as sublancin itself. This established that the His-Tag did not interfere with the biological activity of the sublancin peptide.

EXAMPLE 6

Recovery of Sublancin-Gly-His-Tag Directly From Culture Supernatant.

One of the primary reasons for attaching a His-Tag to a polypeptide is to facilitate its recovery and purification from complex mixtures. To fulfill this purpose, it was determined whether the Sublancin-His Tag could be recovered directly from a culture supernatant on a Ni-NTA column without first subjecting it to a preliminary purification procedure such as the Hydrophobic Interaction column. Such a recovery method provides a more economical method of manufacture of sublancin, and facilitates a more wide-scale utilization of sublancin.

To explore this question, the *B. subtilis* 168 mutant that contained the gene for the Sublancin 3×Gly-6×His prepeptide was expressed as described above. After 26 hr of growth, the culture was centrifuged to remove the cells, and the complete culture supernatant was applied directly to the Ni-NTA column using the same loading conditions as above. The column was washed, and then eluted with 350 mM imidazole, lyophilized, and HPLC-purified as above. The purified fractions were subjected to MALDI-TOF mass spectral analysis. The results indicated that the same spectrum of Sublancin-His Tagged species were recovered, and these species were recovered in the same amounts by this procedure as in the procedure that employed the Hydrophobic Interaction column prior to the Ni-NTA column. Moreover, the level of purification was the same by means of the Ni-NTA column alone, as with the two-column procedure. It was concluded that the His-tagged sublancin can, indeed, be recovered in a single purification step directly from the culture supernatant by capturing it on a Ni-NTA column.

Reference List

1. Liu, W. and J. N. Hansen. 1991. Conversion of *Bacillus subtilis* 168 to a subtilin producer by competence transformation. J. Bacteriol. 173:7387–7390.

2. Liu, W. and J. N. Hansen. 1992. Enhancement of the chemical and antimicrobial properties of subtilin by site-directed mutagenesis. J. Biol. Chem. 267:25078–25085.

3. Paik, S. H., A. Chakicherla, and J. N. Hansen. 1998. Identification and characterization of the structural and transporter genes for, and the chemical and biological properties of, sublancin 168, a novel lantibiotic produced by *Bacillus subtilis* 168. J. Biol. Chem. 273:23134–23142.

4. Rodriguez, V. W. 1999. thesis. University of Maryland. Ph. D. Thesis. The Characterization of the Downstream Border of the Subtilin Operon in *Bacillus subtilis* LH45; and an Investigation of the Cellular Target of the Lantibiotic Sublancin Produced by *Bacillus subtilis* 168.

5. Sloma, A., C. F. Rudolph, G. A. Rufo Jr, B. J. Sullivan, K. A. Theriault, D. Ally, and J. Pero. 1990. Gene encoding a novel extracellular metalloprotease in *Bacillus subtilis*. J. Bacteriol. 172:1024–1029.

6. Young, F. E. and G. A. Wilson. 1974. *Bacillus subtilis*, p. 69–114. In R. C. King (ed.), Handbook of Genetics. Plenum Press, New York.

7. Vary, J. C. and H. O. Halvorson. 1965. Kinetics of germination of Bacillus spores. J. Bacteriol. 89:1340–1347.

8. Kussman, M., E. Nordhoff, H. Rahbek-Nielsen, S. Haebel, M. Rossel-Larsen, L. Jakobsen, J. Gobom, E. Mirgorod-Skaya, A. Kroll-Kristensen, L. Palm, and P. Roepstorff. June, 1997. Matrix-assisted laser desorption/ionization mass spectrometry sample preparation techniques designed for various peptide and protein analytes. J. Mass spectrum. 32:593–601.

What is claimed:

1. An affinity-tag labeled sublancin peptide comprising a chimeric polypeptide comprising a sublancin peptide, an amino acid spacer attached to the C-terminus of the sublancin peptide, and an affinity tag attached to the spacer, wherein the sublancin peptide comprises amino acid residues 1–37 of SEQ ID No. 2.

2. The affinity-tag labeled sublancin peptide of claim 1, wherein the sublancin peptide is obtained from *Bacillus subtilis*.

3. The affinity-tag labeled sublancin peptide of claim 2, wherein the sublancin peptide is obtained from *Bacillus subtilis* strain 168.

4. The affinity-tag labeled sublancin peptide of claim 1, wherein the spacer comprises from 1 to 15 amino acid residues.

5. The affinity-tag labeled sublancin peptide of claim 1, wherein the spacer comprises about 2–5 amino acid residues.

6. The affinity-tag labeled sublancin peptide of claim 1, wherein the affinity tag comprises from 2–10 histidine residues.

7. The affinity-tag labeled sublancin peptide of claim 6, wherein the affinity tag comprises from 2–6 histidine residues.

8. The affinity-tag labeled sublancin peptide of claim 7, wherein the affinity tag comprises about 6 histidine residues.

9. A method of purifying an affinity-tag labeled sublancin peptide from a solution, the peptide comprising a sublancin peptide, an amino acid spacer attached to the C-terminus of the sublancin peptide, and an affinity tag attached to the spacer, and wherein the method comprises contacting the peptide with a solid support having an affinity for the affinity tag, and wherein the sublancin peptide comprises amino acid residues 1–37 of SEQ ID No. 2.

10. The method of claim 9, wherein the spacer comprises from 1–15 amino acid residues.

11. The method of claim 9, wherein the affinity tag comprises from 2–10 histidine residues.

12. The method of claim 9, wherein the solid support is a nickel-coated plastic or magnetic bead.

13. A method for decontaminating a gram positive bacterial spore-infected area comprising treating the infected area with a spore-inhibiting effective amount of a peptide according to claim 1.

14. The method of claim 13, wherein the spore-inhibiting effective amount of the sublancin protein is 0.01 µg/ml to 10 µg/ml.

15. The method of claim 13, wherein the bacterial spore is from at least one of *Bacillus, Enterococcus, Lactococcus, Listeria* and *Staphylococcus*.

16. The method of claim 15, wherein the bacterial spore is from *Bacillus anthrasis*.

* * * * *

SEQUENCE LISTING

<160> NUMBER OF SEQ ID NOS: 3

<210> SEQ ID NO 1
<211> LENGTH: 2517
<212> TYPE: DNA
<213> ORGANISM: Artificial Sequence
<220> FEATURE:
<223> OTHER INFORMATION: EcoRI-HindIII insert of the pLPVc integrative
      plasmid.

<400> SEQUENCE: 1

```
gaattccggc tctaaagcga ttctgagagc agtttcttat acaccagcag gaactgcact      60
tcaacgagct ggattaacag gtgggcataa gagttaagat aaatttaaac ttatataaca     120
catcgcttaa agtttttttg ttttaaaaac ttaaaaaaca tggtaaaatt atataaaaac     180
ataagaaaga gtgattatat ggaatatgta gttatgataa tcatttattt agcactttc     240 tttattttta ctgttttcct aaatacacgt tatagtttg atgaaaaatg cttagtctta     300
aaatttggtt tatctaaaac agaaattcca attaatcaaa tagttagtat taaagagtca     360
gacaagtatg gagttgcaga taatatcgat tataaaattg gtatgccata tgctcaacca     420
gatagaattg ttattgaaac tacaaataag cgttttctag tttttttaaa tggagctcaa     480
caatttattc aaaagtataa aagggttagt gtttgaacat aaaaaagtac cttcttacaa     540
tagaaggtac tttttttgtat ctataattat taaaaattta cctaaatttt tatcattatt     600
aattcaaaat aaatccataa tagtcaattt tatttagtgt attacaacca attcggatcc     660
aagcacccat tagttcaaca aacgaaaatt ggataaagtg ggatatttt aaaatatata     720 tttatgttac agtaatattg acttttaaaa aaggattgat tctaatgaag aaagcagaca     780
agtaagcctc ctaaattcac tttagataaa aatttaggag gcatatcaaa tgaactttaa     840
```

-continued

```
taaaattgat ttagacaatt ggaagagaaa agagatattt aatcattatt tgaaccaaca    900
aacgactttt agtataacca cagaaattga tattagtgtt ttataccgaa acataaaaca    960
agaaggatat aaattttacc ctgcatttat tttcttagtg acaagggtga taaactcaaa   1020
tacagctttt agaactggtt acaatagcga cggagagtta ggttattggg ataagttaga   1080
gccactttat acaattttttg atggtgtatc taaaacattc tctggtattt ggactcctgt   1140
aaagaatgac ttcaaagagt tttatgattt atacctttct gatgtagaga aatataatgg   1200
ttcggggaaa ttgtttccca aaacaccat acctgaaaat gcttttctc tttctattat   1260
tccatggact tcatttactg ggtttaactt aaatatcaat aataatagta attaccttct   1320
acccattatt acagcaggaa aattcattaa taaaggtaat tcaatatatt taccgctatc   1380
tttacaggta catcattctg tttgtgatgg ttatcatgca ggattgttta tgaactctat   1440
tcaggaattg tcagataggc ctaatgactg gctttttataa tatgagataa tgccgactgt   1500
acttttttaca gtcggttttc taatgtcact aacctgcccc gttagttgaa aagggattc   1560
gtgtattaca accaattctg tttattgata ggtaataaag ttttttttct atgatttatg   1620
aacaagtttc cttataattt tcaaaaaaaa ataaaaaata tggttgaatt tagatttatc   1680
ttcctttata ttaaaaaatg taatccggat tgcaaacaaa tggggaggtt ttacaaatgg   1740
aaaagctatt taagaagtt aaactcgagg aactcgaaaa ccaaaaaggt agtggattag   1800
gaaaagctca gtgtgctgcg ttgtggctac aatgtgctag tggcggtaca attggttgtg   1860
gtggcggagc tgttgcttgt caaaactatc gtcaattctg cagataaaac atttgtagag   1920
ggaatatttt aaatattccc tcatatttaa agcggggatt gaaattgaat aagaaaaaga   1980
aatatgttca tactaaacag tttaatagtc atgattgtgg actagcttgt atctcgtcaa   2040
ttttaaagtt tcataacctt aactatggaa ttgatttctt actagaccta attggggata   2100
aggaaggcta tagtttaaga gacttaattg ttattttttaa gaagatgggg ataaaaacta   2160
ggccacttga attgcaagaa aataagacat tcgaagccct aaaacaaata aagctcccctt   2220
gtatagcttt gttagaaggg gaggaatatg gacattacat aacaatatac gaaattagaa   2280
ataactattt acttgttagt gatcctgata agacaaaat aactaaaata aaaaaagagg   2340
attttgaaag taaattcaca aactttatat tagaaattga caaagagtca attcctgaaa   2400
aagaaaaaga tcaaaaaaaa cattcttact ttttttaagga catactttt agaaataaat   2460
tgatcgtttt tgtgattttta ttgacttcct tgttcgttgt gggtcttgct gaagctt     2517
```

<210> SEQ ID NO 2
<211> LENGTH: 300
<212> TYPE: DNA
<213> ORGANISM: Artificial Sequence
<220> FEATURE:
<223> OTHER INFORMATION: The sublancin-His Tag gene and its corresponding peptide sequence.
<221> NAME/KEY: CDS
<222> LOCATION: (1)..(300)
<223> OTHER INFORMATION:

<400> SEQUENCE: 2

```
atg gaa aag cta ttt aaa gaa gtt aaa ctc gag gaa ctc gaa aac caa     48
Met Glu Lys Leu Phe Lys Glu Val Lys Leu Glu Glu Leu Glu Asn Gln
1               5                   10                  15 aaa ggt agt gga tta gga aaa gct cag tgt gct gcg ttg tgg cta caa     96
Lys Gly Ser Gly Leu Gly Lys Ala Gln Cys Ala Ala Leu Trp Leu Gln
            20                  25                  30
```

-continued

```
tgt gct agt ggc ggt aca att ggt tgt ggt ggc ggc gcc gtt gct tgt    144
Cys Ala Ser Gly Gly Thr Ile Gly Cys Gly Gly Gly Ala Val Ala Cys
        35                  40                  45 caa aac tat cgt caa ttc tgt aga ggt ggt ggt ggg gga ggc ggg gga    192
Gln Asn Tyr Arg Gln Phe Cys Arg Gly Gly Gly Gly Gly Gly Gly Gly
    50                  55                  60 ggg ggt ggt ggt gga gga ggt ggt ggt ggt ggt atg tca aag ttc        240
Gly Gly Gly Gly Gly Gly Gly Gly Gly Gly Gly Met Ser Lys Phe
65                  70                  75                  80 gat gat ttc gat cta gat gtt gtg aaa gtc tct aaa caa gac tca aaa    288
Asp Asp Phe Asp Leu Asp Val Val Lys Val Ser Lys Gln Asp Ser Lys
                85                  90                  95 atc act ccg caa                                                    300
Ile Thr Pro Gln
            100
```

<210> SEQ ID NO 3
<211> LENGTH: 100
<212> TYPE: PRT
<213> ORGANISM: Artificial Sequence
<220> FEATURE:
<223> OTHER INFORMATION: The peptide sequence for sublancin-His Tag.

<400> SEQUENCE: 3

```
Met Glu Lys Leu Phe Lys Glu Val Lys Leu Glu Glu Leu Glu Asn Gln
1               5                   10                  15

Lys Gly Ser Gly Leu Gly Lys Ala Gln Cys Ala Ala Leu Trp Leu Gln
            20                  25                  30

Cys Ala Ser Gly Gly Thr Ile Gly Cys Gly Gly Gly Ala Val Ala Cys
        35                  40                  45

Gln Asn Tyr Arg Gln Phe Cys Arg Gly Gly Gly Gly Gly Gly Gly Gly
    50                  55                  60

Gly Gly Gly Gly Gly Gly Gly Gly Gly Gly Met Ser Lys Phe
65                  70                  75                  80

Asp Asp Phe Asp Leu Asp Val Val Lys Val Ser Lys Gln Asp Ser Lys
                85                  90                  95

Ile Thr Pro Gln
            100
```